United States Patent [19]

Singer

[11] Patent Number: 5,389,217

[45] Date of Patent: Feb. 14, 1995

[54] MEASUREMENT OF BLADDER OXYGEN

[75] Inventor: Mervyn Singer, London, England

[73] Assignee: Biomedical Sensors Ltd., High Wycombe, England

[21] Appl. No.: 234,083

[22] Filed: Apr. 28, 1994

[51] Int. Cl.$^6$ .................. G01N 27/26; A61B 5/05; A61M 29/00

[52] U.S. Cl. .................. 204/153.17; 204/153.16; 204/153.12; 204/415; 128/635; 128/639; 604/96

[58] Field of Search .............. 204/415, 153.12, 153.16, 204/153.17, 153.1; 128/635, 637, 639, 656, 657, 658; 604/96

[56] References Cited

U.S. PATENT DOCUMENTS

| | | | |
|---|---|---|---|
| 3,905,888 | 9/1975 | Mindt et al. | 204/415 |
| 4,838,269 | 6/1989 | Robinson et al. | 604/96 |
| 5,262,037 | 11/1993 | Markle et al. | 204/415 |
| 5,312,344 | 5/1994 | Grinfeld | 604/96 |

Primary Examiner—John Niebling
Assistant Examiner—Bruce F. Bell
Attorney, Agent, or Firm—Peter C. Richardson; Lawrence C. Akers; Mark Dryer

[57] ABSTRACT

An apparatus for the determination and continuous monitoring of bladder epithelial oxygen (pbO$_2$) which comprises, in combination, an introductory catheter with an inflatable placement cuff and an oxygen sensor, wherein the sensor is completely accommodated within the catheter when not in use and, when the apparatus is placed within a patient's bladder, the sensor is adapted to be deployed so that the distal end of the sensor passes through an open port in the distal wall of the catheter and extends beyond the tip of the catheter to rest against the wall of the bladder; and a method for the continuous monitoring of pbO$_2$ using such apparatus.

5 Claims, 2 Drawing Sheets

MEASUREMENT OF BLADDER OXYGEN

FIELD OF THE INVENTION

This invention relates to an apparatus and method for the measurement of bladder oxygen. More particularly, the invention is concerned with the monitoring of bladder epithelial oxygen tension, especially in patients suffering from, or in risk of, shock, as a diagnostic tool to track changes in organ perfusion.

BACKGROUND OF THE INVENTION

U.S. Pat. No. 3,905,888 discloses an electrochemical sensor for the in vivo determination of oxygen partial pressure in biological media, particularly blood.

Methods for the continuous measurement of oxygen partial pressure are known in the art for patients under intensive care treatment for various conditions of respiratory and cardiovascular failure, including hypoperfusion and vasoconstriction. A clinically practical and technically fully-developed blood gas measuring sensor is available as the Continucath 1000 ™ system manufactured and marketed by Biomedical Sensors Ltd. of High Wycombe, England.

The system includes an electrochemical sensor contained within a catheter having a wall of oxygen-permeable polymeric material which acts as a diffusion membrane. The structure of the sensor is similar to, but an improvement on, the structure of the sensor disclosed in U.S. Pat. No. 3,905,888. The distal end of the catheter is adapted to be inserted in a patient's artery, usually in the arm, and the system is activated immediately following connection of the proximal end of the catheter, via a suitable electrical connector, to a monitor.

The system provides continuous monitoring of intravascular $pO_2$ and is an effective indicator of hypoxic and hyperoxic conditions.

Systems have also been proposed for the in vivo measurement and monitoring of other parameters in a patient's blood. A particularly effective system is the Paratrend 7 ™ system developed by Biomedical Sensors Ltd., which includes a multiparameter catheter comprising sensors for the determination of $pO_2$, $pCO_2$, pH and temperature.

The oxygen sensor used in the multi-parameter catheter may be an electrochemical sensor similar to that used in the commercially available Continucath 1000 ™, but with certain improvements such as those described and claimed in U.S. Pat. No. 5,262,037 or patent application Ser. No. 08/095232.

While the determination of blood $pO_2$, for conditions where ventilation support is indicated, is performed effectively by the Continucath 1000 ™ and Paratrend 7 ™ systems inserted in a patient's artery, there are some conditions where an alternative or additional site of measurement, particularly for measuring regional perfusion, is indicated. Thus, it has been postulated that urine oxygen may track kidney oxygen tension and some studies have been performed, with inconclusive results. Also, it is theorized that bladder perfusion behaves similarly to organs like the gastrointestinal tract, skin and kidney, in that blood flow is diverted from the bladder to more critical organs during shock. Bladder $pO_2$, more strictly bladder epithelial $pO_2$, indicated hereinafter as $pbO_2$ responds more quickly to hemodynamic variations than urine $pO_2$ as a relatively non-invasive early indicator of poor organ perfusion with a view to provide an early warning, leading to prevention or earlier treatment, of multiple organ failure.

Surprisingly it has now been found from rat models that $pbO_2$ changes rapidly in relation to the circulatory status of the animal and provides a reliable indication of concurrent changes in systemic blood pressure (BP), aortic (ABF) and renal (RBF) blood flow.

SUMMARY OF THE INVENTION

In accordance with the present invention there is provided an apparatus for the determination and continuous monitoring of bladder epithelial oxygen ($pbO_2$) which comprises, in combination, an introductory catheter and an oxygen sensor, wherein said catheter comprises an elongated hollow tube having channels therein, a proximal end and a distal end, which distal end forms a tip having an open port at or near the distal termination thereof and inflatable placement means located proximal to the open port, each of said channels terminating in a port at the proximal end of the catheter, a first port is connected to means for inflating the placement means, a second port is the terminal proximal end of a second channel terminating in the open port in the tip of the catheter and a third port is the terminal proximal end of a drainage channel, said oxygen sensor comprising an elongated sensor having a distal end and a proximal end, said distal end comprising an oxygen-sensing element enveloped within an oxygen-permeable membrane, the sensor is completely accommodated within the second channel of the catheter and, when the apparatus is placed within a patient's bladder, the distal end of the sensor passes through the open port and extends beyond the tip of the catheter, the proximal end of the sensor having a connector attached to a monitor.

Preferably the oxygen-sensing element of the sensor is an electrochemical sensor such as that currently available in the Continucath 1000 ™ or Paratrend 7 ™ systems or the improved sensor described and claimed in U.S. patent application Ser. No. 08/095232. However, other types of oxygen sensor, for example, a fluorescent sensor, may be used.

In a preferred embodiment of the invention the second channel of the catheter which accommodates the oxygen sensor and the drainage channel, each of which terminates in a separate port at the proximal end of the catheter, merge to form a single channel terminating in the open port at or near the distal end of the catheter.

The invention also provides a method for the continuous monitoring of bladder epithelial oxygen ($pbO_2$) which comprises introducing an apparatus as described above into the bladder of a patient, deploying the distal end of the oxygen sensor through the open port in the tip of the catheter so that the sensor extends beyond the tip and rests against the wall of the bladder, inflating the placement means so that the apparatus is held in a desired position within the bladder, connecting the proximal end of the sensor to a monitor and obtaining desired readings from the monitor.

BRIEF DESCRIPTION OF THE DRAWINGS

The invention will be more particularly described with reference to the accompanying drawings, in which.

DETAILED DESCRIPTION OF THE INVENTION

The apparatus according to the invention comprises an operative combination of a catheter, which may be considered a modified Foley catheter, and an oxygen sensor. A preferred embodiment of the apparatus is illustrated, in schematic form, in FIG. 3 of the accompanying drawings. The catheter is illustrated separately in FIG. 1 and an enlarged view of the sensor is illustrated in FIG. 2.

Figure 1:
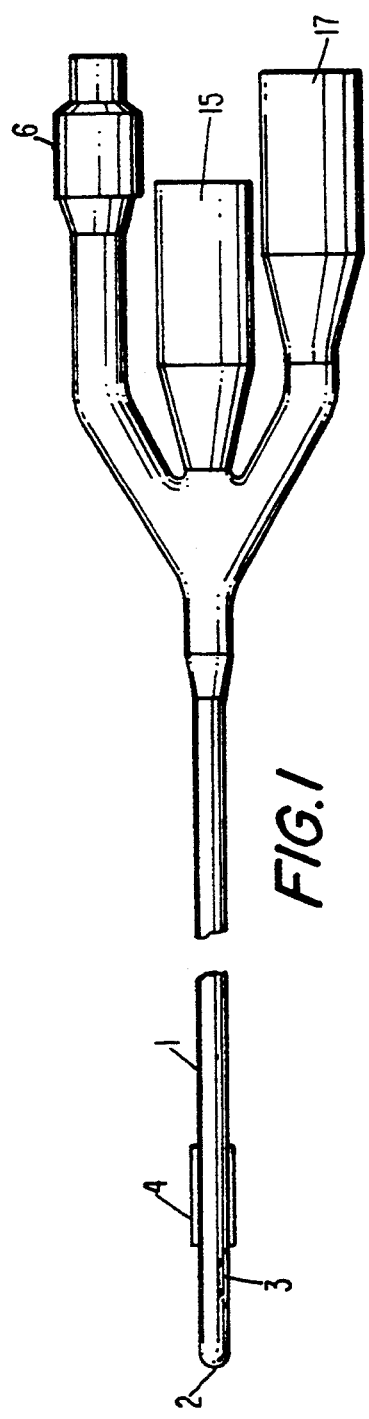
FIG. 1 is a side elevation, in schematic form, of a catheter to be used with a preferred embodiment of an apparatus according to the invention.
Figure 2:
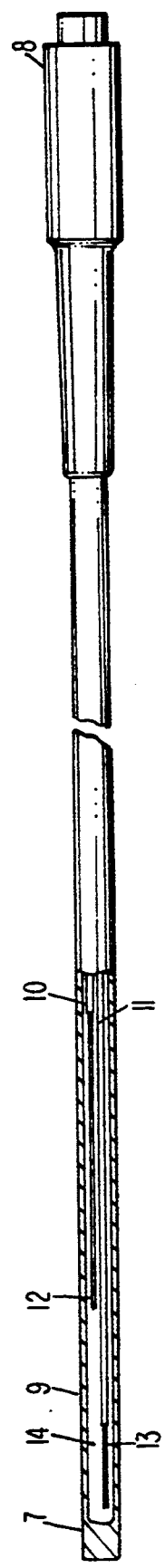
FIG. 2 is a side elevation, somewhat enlarged and partly in section, of an oxygen sensor to be used in the apparatus of the invention.

The catheter illustrated in FIG. 1 comprises an elongated tube 1 terminating in a distal end 2. The distal end defines a tip having an open port 3 near the termination thereof. While the open port may be located at any position near to or at the termination of the tip, in the preferred embodiment illustrated in the drawings it is set back slightly from the termination of the tip for the reason described hereinafter.

Figure 3:
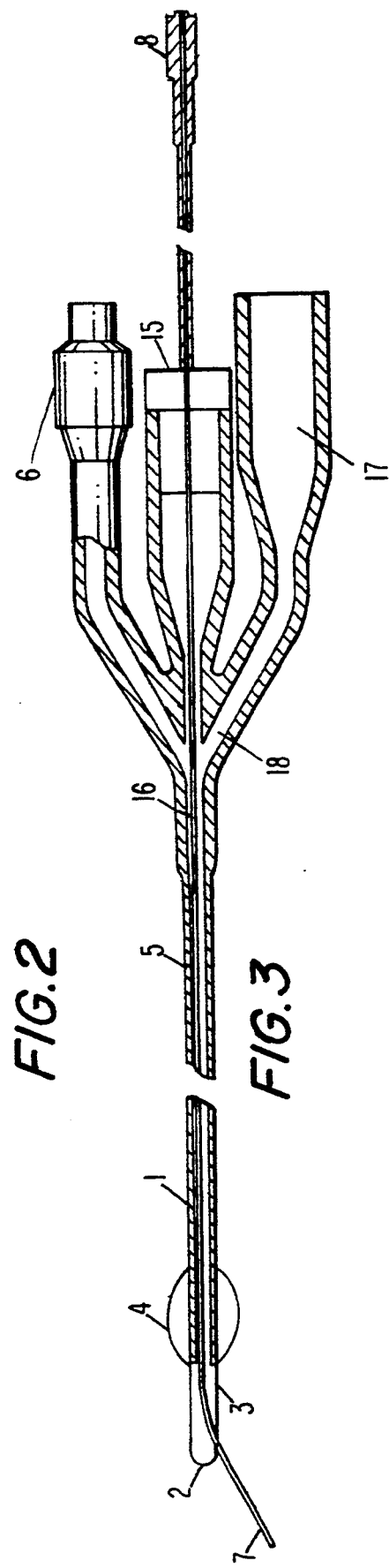
FIG. 3 is a side schematic view of a preferred apparatus according to the invention in an operating condition.

Mounted around the catheter in a location immediately proximal to the open port is an inflatable balloon 4 shown deflated in FIG. 1 and inflated in FIG. 3. The inflatable balloon acts as a placement means and, when the balloon is inflated after the apparatus is introduced into a patient's bladder, allows the apparatus to be held in a desired position within the bladder. An inflatable balloon is the desired placement means but other types of inflatable cuff may be used.

The inflatable placement means is connected through a first channel 5 to a first port 6, located at the proximal end of the catheter, which is adapted to be connected to means for inflating the placement means, for example, a syringe.

A preferred embodiment of an oxygen sensor to be used in the apparatus according to the invention is illustrated in FIG. 2. The sensor has a distal end 7 and a proximal end 8. The portion adjacent the distal end comprises a chamber defined by an oxygen-permeable membrane 9, preferably made of a polymeric material, such as polyethylene. Within the chamber is mounted an oxygen-sensing element which, in the preferred embodiment, comprises two insulated conductors 10, 11 mounted in parallel and having exposed portions comprising, respectively, an anode 12 and a cathode 13. The anode and cathode are immersed in a suitable electrolyte 14. The combination of anode, cathode, electrolyte and membrane form an electrochemical cell for the determination of oxygen partial pressure. Sensors of this type are known in the art and a preferred embodiment is described and claimed in U.S. patent application Ser. No. 08/095,232. In addition to the preferred electrochemical sensor illustrated in FIG. 2, other types of oxygen sensor, for example, a chemical sensor based upon the quenching of a fluorescent oxygen-sensitive indicator, may be used.

Attached to the proximal end 8 of the sensor is a suitable connector adapted to be connected to an appropriate monitor.

The apparatus of the invention is a combination of the catheter and oxygen sensor and to provide the combination, a preferred embodiment of which is illustrated in FIG. 3, the sensor is introduced into the catheter through a second proximal port 15. In the combination apparatus the sensor is accommodated within a second channel 16 of the catheter. As shown in the preferred embodiment of FIG. 3, the second channel passes centrally along the longitudinal axis of the catheter. However, the channel accommodating the sensor may be located eccentrically to the axis or even along or within the wall of the catheter. The second channel carrying the optical sensor terminates at the open port 3 in the tip of the catheter. In the preferred embodiment illustrated in FIG. 3 the terminal part of the second channel is defined by a bend where it meets the exit port 3. The advantage of this configuration is that when the sensor, which is flexible, emerges from the port it extends beyond the catheter at an angle. This facilitates placement of the sensor tip in the epithelial wall of the bladder which provides consistent readings for the epithelial oxygen.

The proximal end of the catheter also has a third port 17 which connects with a drainage channel 18 for the drainage of urine from the bladder. In the embodiment illustrated in FIG. 3, the drainage channel 18 merges with the second channel 16 so that the port 3 may be used for drainage as well as for exit of the sensor. Alternatively, the drainage channel may be separated from the second channel and terminate in an additional port at the distal end of the catheter.

In order to monitor $pbO_2$, an apparatus according to the invention, a preferred embodiment of which is described above, is introduced into the bladder of a patient. The proper positioning of the apparatus within the bladder may be achieved in any standard manner. When the tip of the catheter is properly positioned within the bladder, the distal end of the oxygen sensor is deployed through the open port so that the sensor extends beyond the tip and rests against the wall of the bladder. In this position, the oxygen-permeable membrane enveloping the oxygen-sensing element of the sensor is juxtaposed against the mucosal lining of the bladder and a true reading of the epithelial oxygen may be obtained. The inflatable placement means is then inflated so that the inflatable balloon or cuff rests against the neck of the bladder and the apparatus is held within the bladder. When the sensor/catheter combination is properly positioned the connector at the proximal end of the sensor is connected to an appropriate monitor so that readings providing continuous monitoring of $pbO_2$ may be obtained.

The method of the present invention is predicated upon the fact that the bladder is relatively accessible in the critically ill patient and thus offers a potential site for monitoring regional perfusion, assuming there is a measureable relationship between $pbO_2$ and regional organ perfusion. The following experiments were conducted to test the corelationship between the various measurements.

EXPERIMENTS

Using an apparatus according to the invention, alterations in bladder epithelial oxygen tension ($pbO_2$) were continuously monitored during staged exsanguination and fluid repletion in a rat model. Comparison was made against concurrent changes in systemic blood pressure (BP), aortic blood flow (ABF), renal blood flow (RBF), and arterial blood gas tension (paO$_2$).

An apparatus according to the invention was positioned in accordance with the method described hereinabove in the bladder of each of six spontaneously breathing male Sprague-Dawley rats (wt 164-238 g, median 201 g) anaesthetised with intraperitoneal thiopentone. Doppler flow probes were placed around left renal and abdominal aortic arteries and the carotid artery was cannulated for continuous BP monitoring and blood gas sampling. One ml. boluses of fluid were administered until no change was seen in BP or RBF. The animal was then exsanguinated by 1 ml. aliquots until RBF fell by 50%, then volume-repleted and, finally, exsanguinated to cardiovascular collapse. The results are set out in the following table:

TABLE

|  | Bladder pO$_2$ kPa* | BP mmHg | ABF ml/min | RBF ml/min | PaO$_2$ (kPa) |
|---|---|---|---|---|---|
| (1) Baseline | 9.6 ± 1.7 | 98 ± 5 | 5.9 ± 2.3 | 5.6 ± 0.9 | 11.3 ± 1 |
| (2) 1st filling | 8.7 ± 1.8 | 100 ± 3 | 6.3 ± 2.6 | 5.1 ± 0.6 |  |
| (3) 1st depletion** | 6.5 ± 0.9 | 65 ± 4 | 6.1 ± 1.5 | 2.4 ± 0.3 | 11.3 ± 1.4 |
| (4) 2nd filling | 9.3 ± 1.6 | 84 ± 8 | 6.3 ± 2.2 | 3.6 ± 0.5 | 10.9 ± 2.3 |
| (5) 2nd depl'n-early | 5.2 ± 0.6 | 66 ± 6 | 2.9 ± 1 | 2.5 ± 0.5 |  |
| (6) 2nd depl'n - mid | 3.7 ± 0.9 | 49 ± 8 | 1.2 ± 0.7 | 1.5 ± 0.4 | 12.8 ± 1.4 |
| (7) 2nd depl'n - late | 1.6 ± 0.8 | 12 ± 9 | 0.3 ± 0.1 | 0 ± 0 | 15.3 ± 0.8 |

*1kPascal = 7.500 mm. Hg.
**Exsanguination

Figure 4:
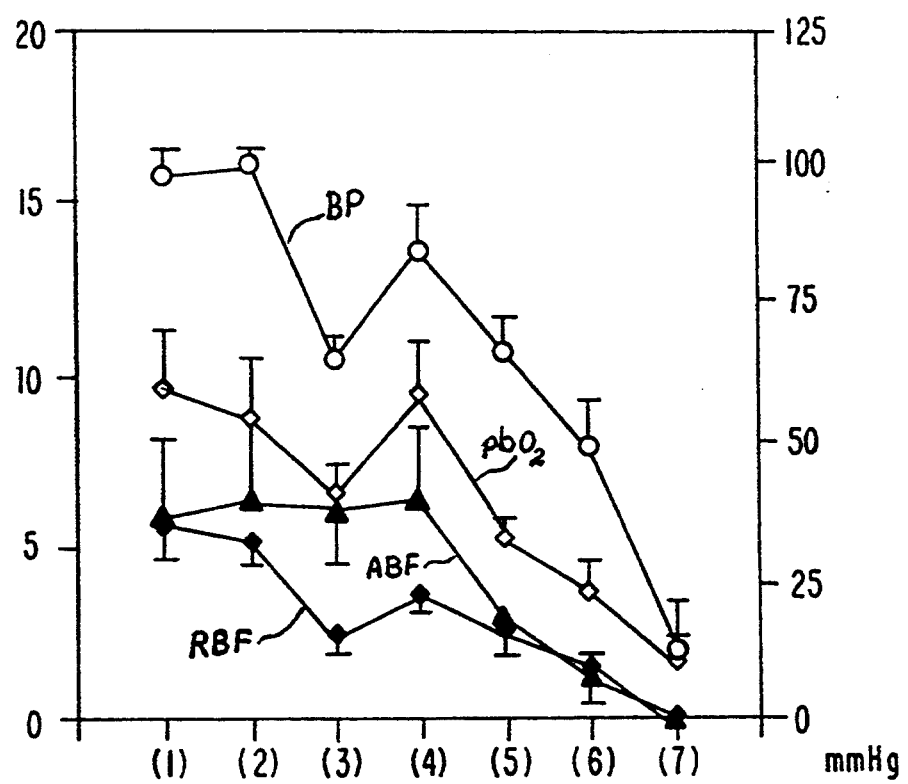
FIG. 4 is a graph illustrating the relationship between concurrent changes in $pbO_2$ and systemic blood pressure (BP), aortic blood flow (ABF), and renal blood flow (RBF) resulting from experiments on rat models.

The above tabulated results are illustrated graphically in FIG. 4 of the accompanying drawings.

The results from the above experiments show that pbO$_2$ changed rapidly in relation to the circulatory status of the animal. Despite the fall in bpO$_2$, arterial pO$_2$ rose, and pCO$_2$ fell, due to hyperventilation secondary to the increasing metabolic acidosis.

The results of the experiments indicate that the method according to the invention provides a useful means for assessing regional organ perfusion.

I claim:

1. An apparatus for the determination and continuous monitoring of bladder epithelial oxygen (pbO$_2$) which comprises, in combination, an introductory catheter and an oxygen sensor, wherein said catheter comprises an elongated hollow tube having channels therein, a proximal end and a distal end, which distal end forms a tip having an open port at or near the distal termination thereof and inflatable placement means located proximal to the open port, each of said channels terminating in a port at the proximal end of the catheter, a first port is connected to means for inflating the placement means, a second port is the terminal proximal end of a second channel terminating in the open port in the tip of the catheter and a third port is the terminal proximal end of a drainage channel, said oxygen sensor comprising an elongated sensor having a distal end and a proximal end, said distal end comprising an oxygen-sensing element enveloped within an oxygen-permeable membrane, the sensor is completely accommodated within the second channel of the catheter and, when the apparatus is placed within a patient's bladder, wherein the distal end of the sensor passes through the open port and extends beyond the tip of the catheter, the proximal end of the sensor having a connector attached to a monitor.

2. An apparatus according to claim 1, in which the inflatable placement means is an inflatable balloon.

3. An apparatus according to claim 1, in which the second channel of the catheter which accommodates the oxygen sensor, and the drainage channel, each of which terminates in a separate port at the proximal end of the catheter, merge to form a single channel terminating in the open port at or near the distal end of the catheter.

4. An apparatus according to claim 1, in which the oxygen-sensing element of the oxygen sensor comprises two insulated conductors mounted in parallel within a chamber defined by a polyethylene membrane and having exposed distal portions comprising, respectively, an anode and a cathode, immersed in an electrolyte.

5. A method for the continuous monitoring of bladder epithelial oxygen (pbO$_2$) which comprises introducing into the bladder of a patient an apparatus comprising, in combination, an introductory catheter and an oxygen sensor, wherein said catheter comprises an elongated hollow tube having channels therein, a proximal end and a distal end, which distal end forms a tip having an open port at or near the distal termination thereof and inflatable placement means located proximal to the open port, each of said channels terminating in a port at the proximal end of the catheter, a first port be connected to means for inflating the placement means, a second port is the terminal proximal end of a second channel terminating in the open port in the tip of the catheter and a third port is the terminal proximal end of a drainage channel, said oxygen sensor comprising an elongated sensor having a distal end and a proximal end, said distal end comprising an oxygen-sensing element enveloped within an oxygen-permeable membrane, the sensor is completely accommodated within the second channel of the catheter, deploying the distal end of the oxygen sensor through the open port in the tip of the catheter so that the sensor extends beyond the tip and rests against the wall of the bladder, inflating the placement means so that the apparatus is held within the bladder, connecting the proximal end of the sensor to a monitor and obtaining desired readings from the monitor.

* * * * *